(12) United States Patent
Aharon et al.

(10) Patent No.: US 8,626,690 B2
(45) Date of Patent: Jan. 7, 2014

(54) PATTERN RECOGNITION

(75) Inventors: Michal Aharon, Haifa (IL); Ira Cohen, Modiin (IL); Ruth Bergman, Haifa (IL); Doron Shaked, Kirayat Tivon (IL)

(73) Assignee: Hewlett-Packard Development Company, L.P., Houston, TX (US)

( * ) Notice: Subject to any disclaimer, the term of this patent is extended or adjusted under 35 U.S.C. 154(b) by 374 days.

(21) Appl. No.: 13/033,443

(22) Filed: Feb. 23, 2011

(65) Prior Publication Data
US 2012/0215736 A1 Aug. 23, 2012

(51) Int. Cl.
*G06N 5/02* (2006.01)

(52) U.S. Cl.
USPC .......................................................... 706/46

(58) Field of Classification Search
None
See application file for complete search history.

(56) References Cited

U.S. PATENT DOCUMENTS

| | | | |
|---|---|---|---|
| 6,618,725 B1 | 9/2003 | Fukuda et al. | |
| 6,826,569 B2 | 11/2004 | Robertson | |
| 7,415,461 B1 * | 8/2008 | Guha et al. | 1/1 |
| 2005/0289401 A1 * | 12/2005 | Goin et al. | 714/47 |
| 2007/0282785 A1 * | 12/2007 | Fayyad et al. | 707/1 |
| 2009/0006290 A1 | 1/2009 | Gunawardana et al. | |
| 2009/0083222 A1 * | 3/2009 | Craswell et al. | 707/3 |
| 2009/0124507 A1 | 5/2009 | Sun et al. | |
| 2009/0157643 A1 | 6/2009 | Gollapudi et al. | |
| 2010/0185649 A1 | 7/2010 | Zhou et al. | |
| 2012/0136855 A1 * | 5/2012 | Ni et al. | 707/724 |

OTHER PUBLICATIONS

Craswell et al, Random Walks on the Click Graph, 2007.*
Deng et al, A Generalized Co-HITS Algorithm and its Application to Bipartite Graphs, 2009.*
Dogrusoz et al, On labeling in graph visualization, 2007.*
Schulz et al, Visual Analysis of Bipartite Biological Networks, 2008.*
International Search Report, PCT/US2011/026722, Feb. 28, 2012, 9 pages.
Y. Chen, et al.; "Application of Distributed Safe Log Management in Small-scale, High-risk System"; Feb. 26-28, 2010; pp. 427-429; vol. 1; http://ieeexplore.ieee.org/Xplore/login.jsp?url=http://ieeexplore.ieee.org/ iel5/5445099/5451211/05451919.pdf%3Farnumber%3D5451919&authDecision=203.
Zan Huang, et al.; "Analyzing Consumer-product Graphs: Empirical Findings and Applications in Recommender Systems"; Jul. 2007; pp. 1146-1164; vol. 53; http://citeseerx.ist.psu.edu/viewdoc/summary?doi=10.1.1.67.1856.
Bjorn Scheuermann, et al.; "On the Time Synchronization of Distributed Log Files in Networks with Local Broadcast Media"; Apr. 2009; pp. 431-444; vol. 17; http://portal.acm.org/citation.cfm?id=1552199.
Almudena Konrad, et al.; "Determining Model Accuracy of Network Traces"; Feb. 19, 2006; http://bnrg.cs.berkeley.edu/~adj/publications/paper-files/accuracy-jcss06.pdf.

* cited by examiner

*Primary Examiner* — Jeffrey A Gaffin
*Assistant Examiner* — Mikayla Chubb

(57) ABSTRACT

A method for pattern recognition performed by a physical computing system includes, with the physical computing system, structuring data as a bi-partite graph, a set of instance nodes within the graph representing instances within the data and a set of property nodes within the graph representing properties of the instances, edges between the instance nodes and the property nodes representing values of the properties, assigning a transition probability function to each of the instance nodes and to each of the property nodes, and applying a random walker to the graph, the random walker utilizing the transition probability functions.

15 Claims, 6 Drawing Sheets

600

With a physical computing system, structuring data as a bi-partite graph, a set of instance nodes within the graph representing instances within the data and a set of property nodes within the graph representing properties of the instances, edges between the instance nodes and the property nodes representing values of the properties (block 602)

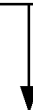

With the physical computing system, assign a transition probability function to each of the instance nodes and to each of the property nodes (block 604)

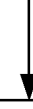

With the physical computing system, applying a random walker to the graph, the random walker utilizing the transition probability functions (block 606)

*Fig. 6*

PATTERN RECOGNITION

BACKGROUND

Various professions often look for patterns in large amounts of data that relates to real life issues. For example, one who studies medicine might look for patterns that indicate a correlation between two physical properties of a patient. Particularly, analyzing large sets of patient data might indicate that individuals who share certain characteristics and past experiences are at risk for particular types of illnesses or other adverse conditions. Finding these patterns in the data provides scientists with additional tools that can help discover causal relationships and thereby find ways to treat such illnesses.

Various techniques such as factor analysis and Principal Component Analysis (PCA) can be used to reduce a number of observable variables within a set of data to a smaller number of unobserved variables that affect the observable variables. Viewing these unobserved variables helps to find patterns within the data. However, such techniques only find patterns that are present within most of the data. In some cases, a pattern may exist within a smaller percentage of the data. Such a pattern would not be picked up by various factor analysis methods.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 6 is a flowchart showing an illustrative method for pattern recognition, according to one example of principles described herein.

Throughout the drawings, identical reference numbers designate similar, but not necessarily identical, elements.

DETAILED DESCRIPTION

Figure 1:
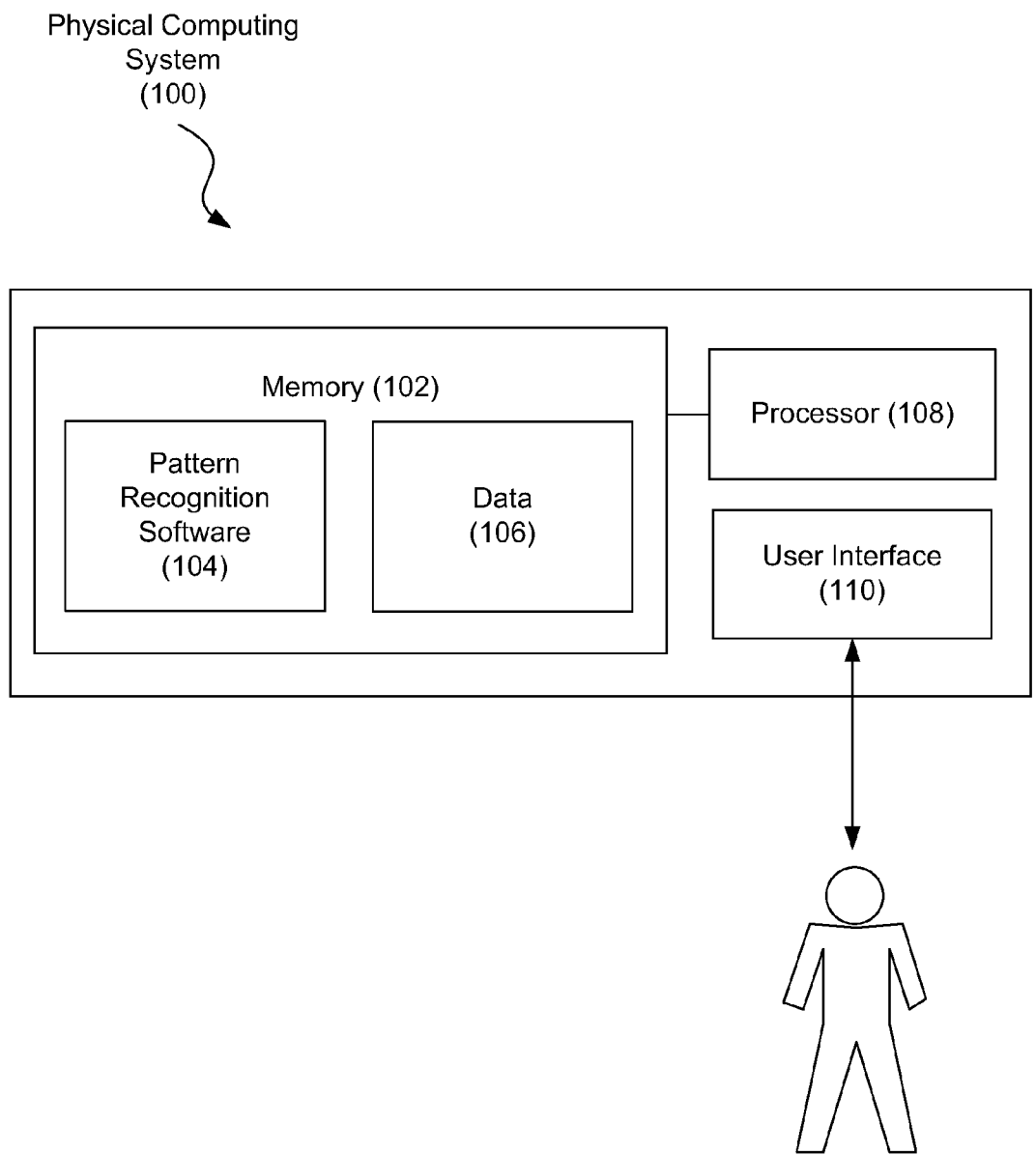
FIG. 1 is a diagram showing an illustrative physical computing system, according to one example of principles described herein.

As mentioned above, various techniques such as factor analysis and Principal Component Analysis (PCA) can be used to reduce a number of observable variables within a set of data to a smaller number of unobserved variables that affect the observable variables. Viewing these unobserved variables helps to find patterns within the data. However, such techniques only find patterns that are present within most of the data. In some cases, a pattern may exist within a smaller percentage of the data. Such a pattern would not be picked up by various factor analysis methods.

In light of this and other issues, the present specification discloses methods and systems for pattern recognition in large amounts of data. Particularly, methods described herein will allow a system to detect patterns that exist within smaller subsets of the available data. A pattern is a non-negligible set of instances that share similar values of similar properties.

According to certain illustrative examples, data that is to be searched for patterns is structured as a bi-partite graph. A bi-partite graph is a type of data structure. A data structure is a way of storing and representing data such that it can be used efficiently. A bi-partite graph data structure includes two sets of nodes. A node in the first set can be connected to any number of the nodes in the second set and vice versa. The connections between nodes are referred to as edges.

To structure the data to allow it to be searched efficiently for patterns, the first set of nodes within the bi-partite graph data structure is used to represent the instances within the data. These nodes will be referred to as instance nodes. The second set of nodes within the data structure is used to represent the properties that may be exhibited by those instances. These nodes will be referred to as property nodes. An edge between a particular instance node and a particular property node is assigned the value of that property associated with that particular instance. For example, if the instance nodes represent persons who have taken a survey and the property nodes represent the questions in that survey, then the edge between an instance node and a property node represents the answer given by the person associated with that instance node to the question associated with that property node.

Each property node is then assigned a transition probability function. The transition probability function assigned to a particular property node is based on the nature of the property associated with that property node. Additionally, each instance node is assigned a transition probability function that varies based on the property nodes connected to that instance node.

A random walker is then applied to the bi-partite graph. The random walker is designed to jump from an instance node to a property node and then from that property node back to an instance node. This process continues for a particular period of time. The edges that the random walker chooses to traverse will be randomly selected according to a computed transition probability function. The transition probability function will cause the random walker to be more likely to traverse certain edges more than others. By looking at the edges that are more frequently traversed, patterns in the data can be revealed.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Referring now to the figures, FIG. 1 is a diagram showing an illustrative physical computing system (100) that can be used for pattern recognition. According to certain illustrative examples, the physical computing system (100) includes a memory (102) having pattern recognition software (104) and data (106) stored thereon. The physical computing system (100) also includes a processor (108) and a user interface (110).

There are many types of memory available. Some types of memory, such as solid state drives, are designed for storage.

These types of memory typically have large storage volume but relatively slow performance. Other types of memory, such as those used for Random Access Memory (RAM), are optimized for speed and are often referred to as "working memory." The various forms of memory may store information in the form of software (104) and data (106).

The physical computing system (100) also includes a processor (108) for executing the software (104) and using or updating the data (106) stored in memory (102). The software (104) may include an operating system. An operating system allows other applications to interact properly with the hardware of the mobile computing system. The other applications may include a pattern recognition application.

A user interface (110) may provide a means for the user (112) to interact with the physical computing system (100). The user interface may include any collection of devices for interfacing with a human user (112). For example, the user interface (110) may include an input device such as a keyboard or mouse and an output device such as a monitor.

Figure 2:
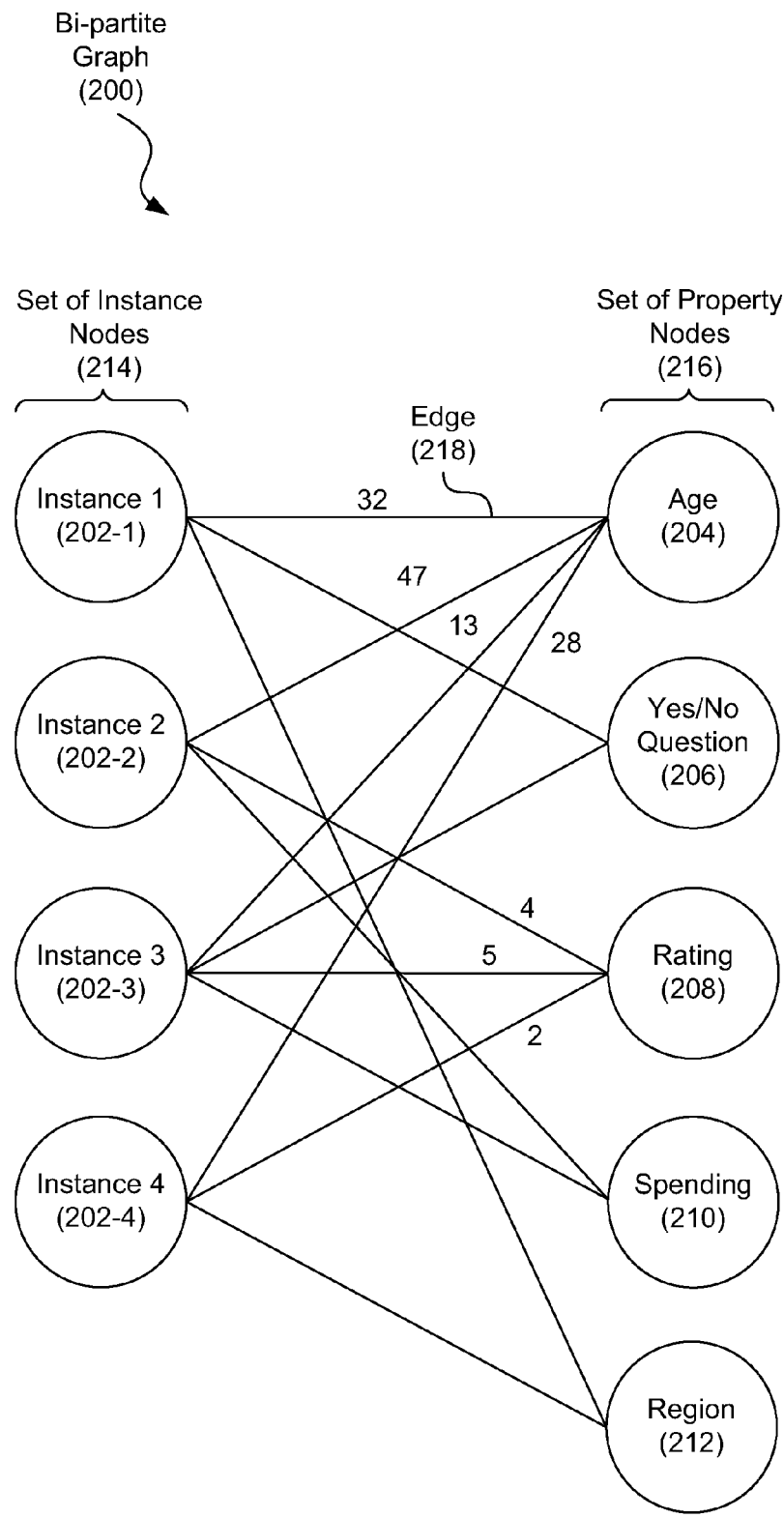
FIG. 2 is a diagram showing an illustrative bi-partite graph, according to one example of principles described herein.

FIG. 2 is a diagram showing an illustrative bi-partite graph (200). As mentioned above, data can be structured as a bi-partite graph (200). Throughout this specification and in the appended claims, the term "bi-partite graph" refers to a data structure and not a visual display. A first set of nodes within the graph (200) will be referred to as instance nodes (214). A second set of nodes within the graph will be referred to as property nodes (216). Edges (218) exist between the instance nodes (214) and the property nodes (216). These edges (218) can be assigned a value.

Each instance node (202) within the bi-partite graph (200) represents one instance within the data. For example, in the case where the data represents results of a survey taken by several people, each instance node will represent one participant of that survey.

Each property node (216) within the bi-partite graph (200) represents a particular property that can be associated with an instance. For example, in the above mentioned example where the data represents results from a survey taken by several people, each property node may represent one question asked in that survey.

The edges (218) within the bi-partite graph (200) are used to indicate the value of each property associated with a particular instance. In some cases, the data may not be complete and thus each instance node (202) may not necessary have an edge (218) connecting to each property node (216). The edges are assigned a value according to the instance node and the property node to which they connect. For example, the edge (218) between instance 1 (202-1) and the age property node (204) is assigned the value of 32. This indicates that the person associated with instance 1 (202-1) is 32 years of age. Likewise, the edge (218) connected between instance 2 (202-2) and the age property node (204) is assigned the value of 47. This indicates that the person associated with instance 2 (202-2) is 47 years of age. Additionally, the value of an edge may include more than one value. For example, an edge may represent a paired value. One of the values in the pair can represent the answer given by a survey participant and the other value can represent the time it took for that participant to give that answer.

The other property nodes (216) represent various other properties. Particularly, the Yes/No question property node (206) may represent a person's response to a yes or no question. The rating property node (208) may represent a person's response to a question asking the person to rate a particular experience on a scale from one to five. The spending property node (210) may represent a person's response to a question regarding how much money he or she spends on a particular day. The region property node (212) may indicate the geographical region of where a person lives. The pattern recognition principles described herein will find patterns among these various properties.

The bi-partite graph (200) shown in FIG. 2 and in the remaining figures is a simple example. A practical bi-partite graph representing a practical set of data will generally be much larger. Thus, the pattern recognition principles described herein will be able to detect patterns in large amounts of complex data.

The various properties represented by the property nodes (216) may be measured in different manners. For example, some properties may contain a large set of discrete values to which a person may belong. For example, if age is measured in years and months, there is a relatively large set of discrete values to represent that age. Conversely, some properties can be measured in a relatively small set of discrete values. For example, the Yes/No question property node (206) may represent a question that can be answered in one of two discrete values, such as an answer to a simple yes or no question. In some cases, the value of an edge may be continuous in nature. This would be the case if the property connected to that edge is one that can take on a continuum of values.

Figure 3:
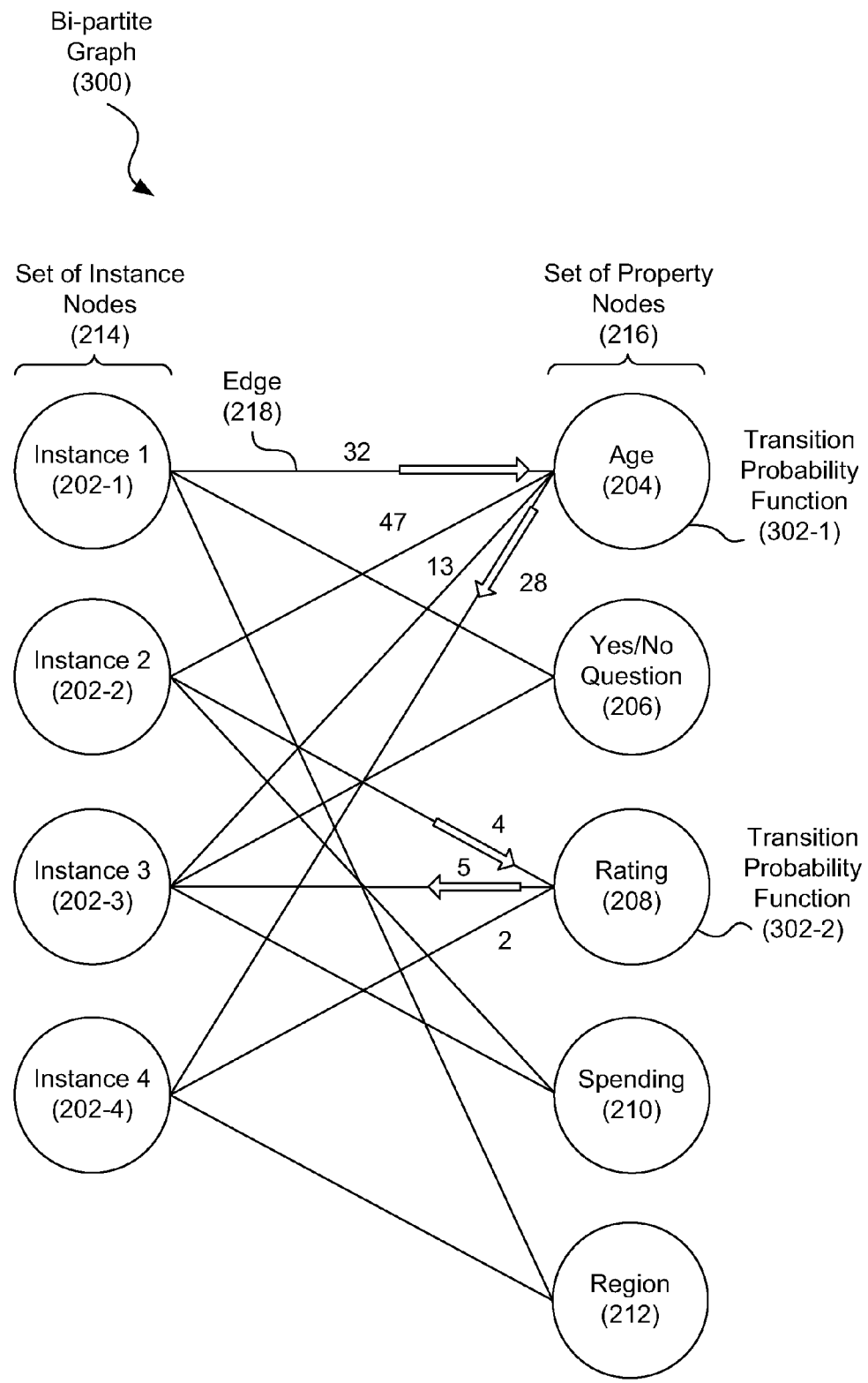
FIG. 3 is a diagram showing the use of transition probability functions for property nodes within a bi-partite graph, according to one example of principles described herein.

FIG. 3 is a diagram showing the use of transition probability functions for property nodes within a bi-partite graph. As mentioned above, a random walker is applied to the bi-partite graph. The random walker will jump from an instance node to a property node and vice versa. It will not, however, jump from an instance node to another instance node. Additionally, it will not jump from a property node to another property node. When the random walker is on a particular property node, it will randomly jump along one of the edges connected from that property node to one of the instance nodes (202). However, the probability it will jump to along a particular edge is not necessarily the same for each edge connected to that property node. A transition probability function assigned to that node will determine the probability that the random walker will jump along each edge (218) connected to that property node.

A probability function is used to define the probability that a random selection of elements within a set will choose a particular element. For example, if a set contains five elements to be chosen at random, then a probability function will describe the probability that each of those five elements will be chosen. The probability that a particular element will be chosen is typically assigned a value between 0 and 1. The adding of the probability assigned to each element within the set will sum to 1. For example, if each of the five elements within the set had an equal chance of being selected, then the probability function would define each element as having a probability of 0.2, the sum of each element being 1. However, a probability function does not necessarily have to assign each element an equal probability of being selected.

The transition probability function assigned to a particular property node treats each edge connected to that property node as an element within a set. Each edge is given a probability according to the transition probability function. The probability assigned to each element is based on the value of the edge from which the random walker arrived. The transition probability function will be such that the random walker is more likely to choose edges with a value similar to that of the arriving edge.

For example, if the random walker jumps from instance node 1 (202-1) to the age property node (204), then the transition probability function (302) assigned to the age property node (204) will determine the probability that the random walker will jump along each edge (218) connected to the age property node (204). The random walker will either jump along the edge connected to instance 2 (202-2), the edge connected to instance 3 (202-3), or the edge connected to instance 4 (202-4). Because the random walker arrived at the age property node (204) from an edge with a value of 32, it will be more likely to leave the age property node (204) on an edge (218) with a value that is closer to 32. Thus, the most likely edge (218) to be traversed is the edge connecting to instance 4 (202-4). This is because the number 28 is closer to the number 32 than the number 47 or the number 13. However, it is still possible that the random walker will jump to instance 2 (202-2) or instance 3 (202-3), but the random walker is less likely to do so.

Each property node (216) may be assigned a unique transition probability function. The transition probability function assigned to a particular property node is dependent upon the nature of that property node. For example, due to the range of values for the age property in the data, a continuous transition probability function (302-1) may be more appropriate for the age property node (204). However, in other cases, the property may only take on a small discrete range of values. For example, the rating property node (206) may represent a question that asks a participant in the survey to rate a particular experience from one to five based on how enjoyable that experience was. Because the edges (218) connected to the rating property node (208) will only take on a small range of values, a discrete transition probability function (302-2) may be more appropriate for the rating property node (208). However, a continuous transition probability function may be used as well.

Using a discrete transition probability function, when the random walker is on the rating property node (208), the random walker will most likely jump to an instance node connected through an edge having a similar value to the edge from which it came. For example, if the random walker arrived from instance node 2 (202-2) along the edge with a value of 4, it will be more likely to leave the rating property node (208) on the edge connected to instance 3 (202-3) than the edge connected to instance 4 (202-4). This is because the value of 5 is closer to the value of 4 than the value of 2.

In some cases, the discrete set of values for a particular property may not have a numerical order. For example, if the property is a person's profession, then the possible set of responses would not be numerically ordered. In this case, the responses may be grouped according to type of profession. The transition probability function may then make it more likely that the random walker will jump to an edge with a profession in the same group.

Figure 4:
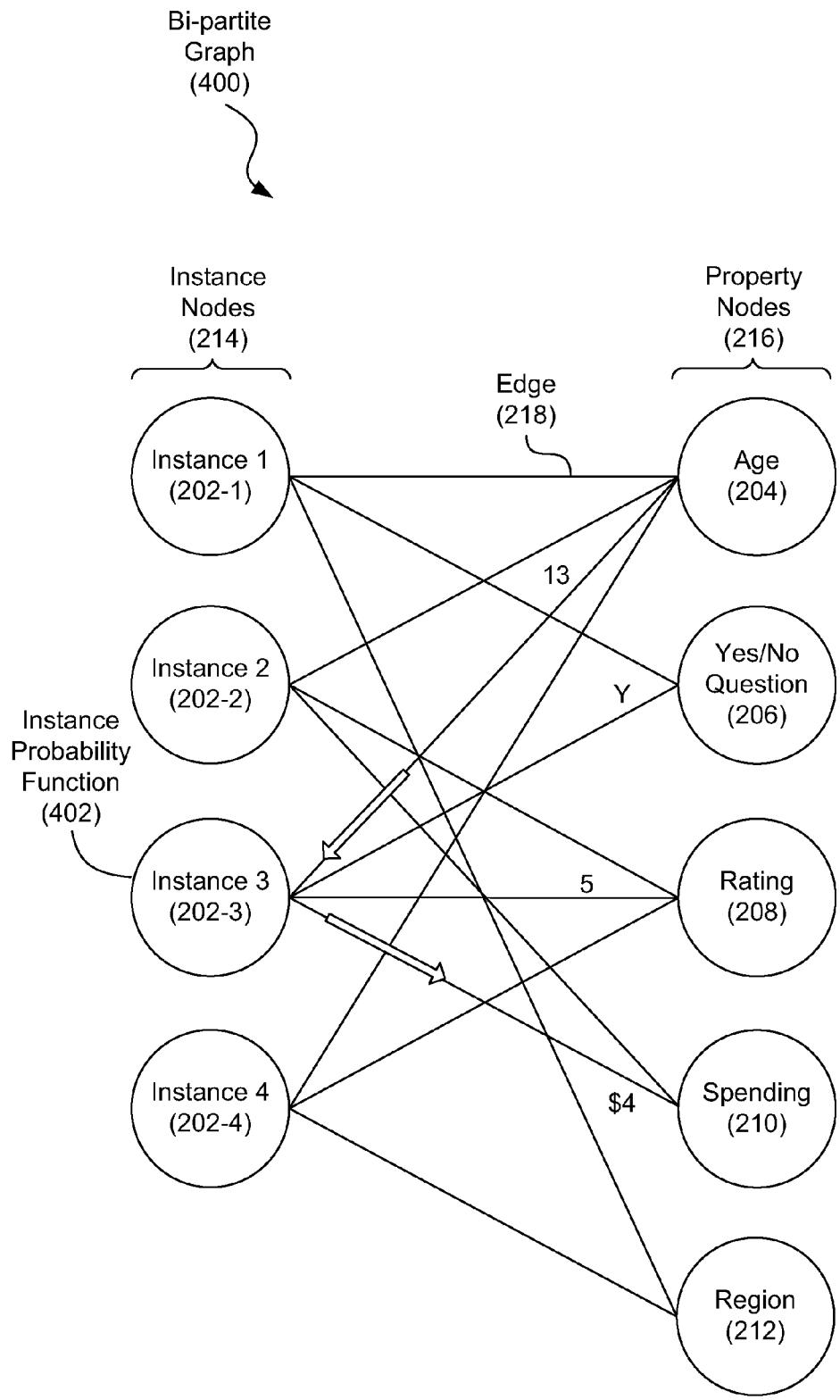
FIG. 4 is a diagram showing the use of a transition probability function for an instance node within a bi-partite graph, according to one example of principles described herein.

FIG. 4 is a diagram showing the use of a transition probability function for an instance node within a bi-partite graph. According to certain illustrative examples, when the random walker arrives at an instance node, the instance transition probability function (402) associated with that instance node determines which edge (218) the random walker will traverse to get to one of the property nodes (216) connected to that instance node (202). In order for the random walker to find patterns in the data, the instance transition probability function associated with each instance node is configured to make it more likely that the random walker will jump to a property node that is correlated to the property node from which it came. This is done by determining how well one property correlates with another property at a particular value. The mechanism for determining how well one property correlates with another will be described in more detail below in the text associated with FIGS. 5A and 5B.

For example, if the random walker arrives at instance node 3 (202-3) from the age property node (204), then the instance probability function (402) associated with instance node 3 (202-3) will make it more likely that the random walker will jump to a property that correlates well with age property at the age of 13. In this example, the pattern recognition system may have previously determined that at the age range around 13 years old, there is a correlation to the spending property (210). This may be because 13 year olds typically do not spend a lot of money per day and thus a number of persons around the age of 13 would be spending similar amounts of money per day. This may not be the case for other age ranges. Thus, the instance probability function will be such that when the random walker is choosing from among the property nodes connected to instance 3 (202-3), it will be more likely to jump to the spending property node (210) than another node which does not correlate well with the age property node (204). It will still be possible for the random walker to jump to a property node that does not correlate well. However, it will be less likely to do so.

Figure 5A:
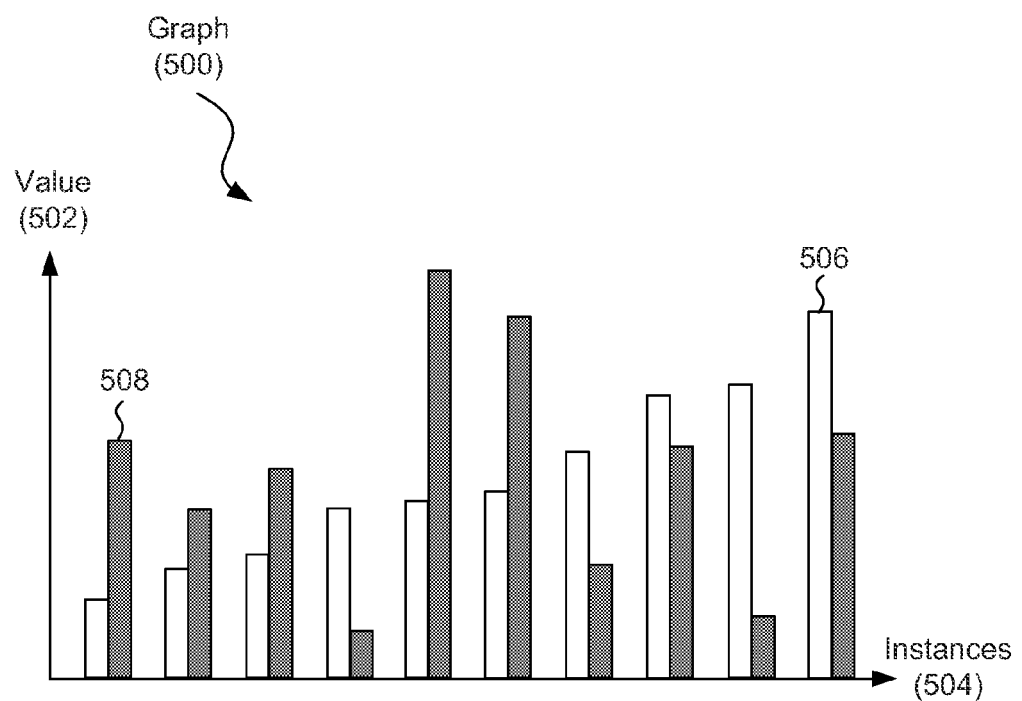
FIGS. 5A and 5B are diagrams showing illustrative graphs that indicate correlation between two different properties, according to one example of principles described herein.
Figure 5B:
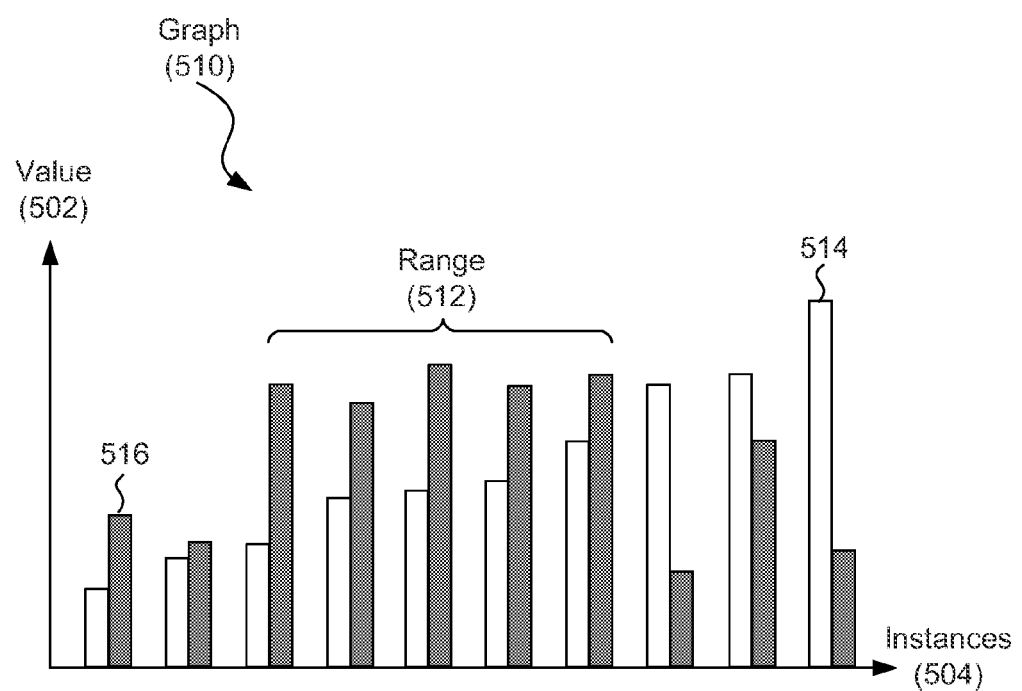

FIGS. 5A and 5B are diagrams showing illustrative graphs that indicate correlation between two different properties. According to certain illustrative examples, the pattern recognition system may determine how well each property correlates with the other properties before applying the random walker function. FIG. 5A illustrates a comparison between two properties that do not correlate well. Alternatively, FIG. 5B illustrates a comparison between two properties that show a correlation at a particular range of values. Each set of bars along the horizontal axis of each graph (500, 510) represents an instance (504) within the data. The vertical length of each graph (500, 510) indicates the value of a particular property. The white bars represent a first property and the shaded bars represent a second property.

To determine how well two properties correlate, the pattern recognition system sorts a first property based on each edge connected to that property node. The edges represent the value of each instance that shares that property. The edges can be sorted in a variety of ways based on the value of the edges. In this example, the edges are sorted from least value to greatest value. The graph (500) in FIG. 5A shows ten different instances. These instances are shown sorted based on their values of the first property represented by the white bars (506). The pattern recognition system can then look at the value of the second property of each of the instances represented by the shaded bars (508). In FIG. 5A, it can be seen that there is no pattern in the second property values represented by the shaded bars (508). The values of the second property are random. Thus, there is little correlation between these two properties.

FIG. 5B illustrates the comparison between two different properties. Again, the instances (504) are sorted based on the value of the first property which is represented by the white bars (514), Here, there is a stability of the values of the second property at a particular range (512) of instances, Thus, the pattern recognition system can determine that there is a correlation between these two properties at the value ranges of the range (512) of instances where stability is found. This correlation can be used to determine how likely the random walker will choose to jump to one property over another.

In some cases, the correlation between each of the properties in the entire bi-partite graph can be predetermined before the random walker function is applied. The transition probability functions for both the instance nodes and the property nodes can also be determined before the random walker function is applied. In some cases, the transition probability functions can be represented by transition matrices. Transition matrices are often used in stochastic system modeling to determine the probability between different outcomes. In some examples, patterns can be found by looking at the stationary vector of a stochastic system. The stationary vector can be determined through application of various mathematical computations on the transition probability matrices. These computations are known in the art and thus a detailed description of them will not be given here.

FIG. 6 is a flowchart showing an illustrative method for pattern recognition. According to certain illustrative examples, the method includes, with a physical computing system, structuring (block 602) data as a bi-partite graph, a set of instance nodes within the graph representing instances within the data and a set of property nodes within the graph representing properties of the instances, edges between the instance nodes and the property nodes representing values of the properties, assigning (block 604) a transition probability function to each of the instance nodes and to each of the property nodes, and applying (block 606) a random walker to the graph, the random walker utilizing the transition probability functions.

In conclusion, through use of methods and systems related to pattern recognition described herein, patterns that are present in a non-negligible number of instances may be revealed. This can allow those who study subjects related to the data to find patterns and relationships that were previously unknown. These patterns and relationships can lead to further research and discovery of new causal relationships.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A method for pattern recognition performed by a physical computing system, the method comprising:
   with said physical computing system, structuring data as a hi-partite graph, a set of instance nodes within said graph representing instances within said data and a set of property nodes within said graph representing properties of said instances, edges between said instance nodes and said property nodes representing values of said properties;
   with said physical computing system, assigning a transition probability function to each of said instance nodes and to each of said property nodes; and
   with said physical computing system, applying a random walker to said graph, said random walker utilizing said transition probability functions;
   in which said transition probability function assigned to each of said property nodes is such that said random walker is more likely to transition between edges closer in value.

2. The method of claim 1, further comprising, with said physical computing system, determining a pattern in said data by determining which of said edges is more frequently traversed by said random walker.

3. The method of claim 1, in which a transition probability function assigned to a property node within said set of property nodes comprises one of a continuous transition probability function based on a property associated with that property node and a discrete transition probability function based on a property associated with that property node.

4. The method of claim 1, in which a transition probability function assigned to a particular instance node within said set of instant nodes comprises a transition probability function configured to make said random walker transition between edges connected to correlated properties.

5. The method of claim 4, in which said correlated properties are correlated at the value of the arriving edge connected to said particular instance node.

6. The method of claim 4, in which it is determined how correlated two properties are by:
   sorting each edge connected to a first property by value;
   sorting each edge connected to a second property based on said sorting of said edges connected to said first property; and
   determining if there is a stability of values at any range within said edges connected to said second property.

7. A physical computing system comprising:
   a processor; and
   a memory communicatively coupled to said processor;
   in which said processor is configured to:
      structure data as a bi-partite graph, a set of instance nodes within said graph representing instances within said data and a set of property nodes within said graph representing properties of said instances, edges between said instance nodes and said property nodes representing values of said properties;
      assign a transition probability function to each of said instance nodes and to each of said property nodes; and
      apply a random walker to said graph, said random walker utilizing said transition probability functions;
      in which said transition probability function assigned to said property node is such that said random walker is more likely to transition between edges closer in value.

8. The system of claim 7, in which said processor is further configured to determine a pattern in said data by determining which of said edges is more frequently traversed by said random walker.

9. The system of claim 7, in which a transition probability function assigned to a property node within said set of property nodes comprises one of: a continuous transition probability function based on a property associated with that property node and a discrete transition probability function based on a property associated with that property node.

10. The system of claim 7, in which a transition probability function assigned to a particular instance node within said set of instant nodes comprises a transition probability function configured to make said random walker transition between edges connected to correlated properties.

11. The system of claim 10, in which said correlated properties are correlated at the value of the arriving edge connected to said particular instance node.

12. The system of claim 10, in which in which to determine how correlated two properties are, said processor is further configured to:
   sort each edge connected to a first property by value;
   sort each edge connected to a second property based on said sorting of said edges connected to said first property; and
   determine if there is a stability of values at any range within said edges connected to said second property.

13. A computer program product for managing providing a layout for graphic objects, said computer program product comprising:
   a computer readable storage device having computer readable code embodied therewith, said computer readable program code comprising:
      computer readable program code configured to structure data as a bi-partite graph, a set of instance nodes within said graph representing instances within said data and a set of property nodes within said graph representing properties of said instances, edges between said instance nodes and said property nodes representing values of said properties;

computer readable program code configured to assign a transition probability function to each of said instance nodes and to each of said property nodes;

computer readable program code configured to apply a random walker to said graph, said random walker utilizing said transition probability functions; and computer readable program code configured to determine a pattern in said data by determining which of said edges is more frequently traversed by said random walker;

in which said transition probability function assigned to each of said instance nodes and property nodes is such that said random walker is more likely to transition between edges closer in value.

14. The computer program product of claim 13, in which said transition probability function assigned to each property node within said set of property nodes comprises one of: a continuous transition probability function based on a property associated with that property node and a discrete transition probability function based on a property associated with that property node.

15. The computer program product of claim 13, in which a transition probability function assigned to a particular instance node within said set of instant nodes comprises a transition probability function configured to make said random walker transition between edges connected to correlated properties.

* * * * *

UNITED STATES PATENT AND TRADEMARK OFFICE
CERTIFICATE OF CORRECTION

Page 1 of 1

PATENT NO. : 8,626,690 B2
APPLICATION NO. : 13/033443
DATED : January 7, 2014
INVENTOR(S) : Michal Aharon et al.

It is certified that error appears in the above-identified patent and that said Letters Patent is hereby corrected as shown below:

In the Claims

In column 7, line 37, in Claim 1, delete "hi-partite" and insert -- bi-partite --, therefor.

In column 7, line 59, in Claim 3, delete "one of" and insert -- one of: --, therefor.

In column 8, line 48, in Claim 12, after "10," delete "in which".

Signed and Sealed this
Sixth Day of May, 2014

Michelle K. Lee
*Deputy Director of the United States Patent and Trademark Office*